United States Patent
Kucklick (10) Patent No.: US 11,730,350 B2
(45) Date of Patent: *Aug. 22, 2023

(54) METHOD OF PROVIDING FOR THE MINIMIZATION OF EXTRAVASATION DURING ARTHROSCOPIC SURGERY

(71) Applicant: Cannuflow, Inc., Scotts Valley, CA (US)

(72) Inventor: Theodore R. Kucklick, Scotts Valley, CA (US)

(73) Assignee: Cannuflow, Inc., Scotts Valley, CA (US)

( * ) Notice: Subject to any disclaimer, the term of this patent is extended or adjusted under 35 U.S.C. 154(b) by 375 days.

This patent is subject to a terminal disclaimer.

(21) Appl. No.: 17/080,680

(22) Filed: Oct. 26, 2020

(65) Prior Publication Data

US 2021/0038246 A1 Feb. 11, 2021

Related U.S. Application Data

(63) Continuation of application No. 16/128,143, filed on Sep. 11, 2018, now Pat. No. 10,813,658, which is a continuation of application No. 14/993,609, filed on Jan. 12, 2016, now Pat. No. 10,070,881, which is a continuation of application No. 13/850,241, filed on Mar. 25, 2013, now Pat. No. 9,233,236, which is a continuation of application No. 13/204,961, filed on Aug. 8, 2011, now abandoned, which is a continuation of application No. 12/542,844, filed on Aug. 18, 2009, now Pat. No. 7,993,299, which is a continuation of application No. 11/213,645, filed on Aug. 19, 2005, now Pat. No. 7,575,565.

(51) Int. Cl.
| | |
|---|---|
| *A61M 1/00* | (2006.01) |
| *A61B 1/015* | (2006.01) |
| *A61B 1/317* | (2006.01) |
| *A61B 17/34* | (2006.01) |
| *A61M 27/00* | (2006.01) |
| *A61B 17/32* | (2006.01) |
| *A61F 13/36* | (2006.01) |
| *A61B 17/00* | (2006.01) |

(52) U.S. Cl.
CPC .............. *A61B 1/015* (2013.01); *A61B 1/317* (2013.01); *A61B 17/320016* (2013.01); *A61B 17/3421* (2013.01); *A61F 13/36* (2013.01); *A61M 27/00* (2013.01); *A61B 2017/00938* (2013.01); *A61B 2217/005* (2013.01); *A61M 1/90* (2021.05)

(58) Field of Classification Search
CPC ......... A61B 1/015; A61B 1/018; A61B 1/317; A61B 17/32; A61B 17/320016
See application file for complete search history.

(56) References Cited

U.S. PATENT DOCUMENTS

| | | | | |
|---|---|---|---|---|
| 6,695,815 B2 * | 2/2004 | Moenning | .......... | A61B 17/3417 604/164.11 |
| 7,993,299 B2 * | 8/2011 | Kucklick | ............... | A61B 1/317 604/35 |

\* cited by examiner

*Primary Examiner* — Laura A Bouchelle (74) *Attorney, Agent, or Firm* — Crockett & Crockett, PC; K. David Crockett, Esq.; Niky Economy Syrengelas, Esq.

(57) ABSTRACT

The devices and methods shown provide for the minimization of extravasation during arthroscopic surgery. The extravasation minimization device allows a surgeon to drain excess fluids from the soft tissue surrounding the surgical field while also providing a stable surgical portal for arthroscopic surgical instruments.

12 Claims, 8 Drawing Sheets

METHOD OF PROVIDING FOR THE MINIMIZATION OF EXTRAVASATION DURING ARTHROSCOPIC SURGERY

This application is a continuation of U.S. application Ser. No. 16/128,143, filed Sep. 11, 2018, which is a continuation of Ser. No. 14/993,609, filed Jan. 12, 2016, now U.S. Pat. No. 10,070,881, which is a continuation of U.S. application Ser. No. 13/850,241, filed Mar. 25, 2013, now U.S. Pat. No. 9,233,236 which is a continuation of U.S. application Ser. No. 13/204,961, filed Aug. 8, 2011, which is a continuation of U.S. application Ser. No. 12/542,844, filed, Aug. 18, 2009, now U.S. Pat. No. 7,993,299, which is a continuation of U.S. application Ser. No. 11/213,645, filed Aug. 19, 2005, now U.S. Pat. No. 7,575,565.

FIELD OF THE INVENTIONS

The inventions described below relate to the field arthroscopic surgery and more specifically, to fluid management during arthroscopic shoulder surgery.

BACKGROUND OF THE INVENTIONS

During minimally invasive surgeries, surgical instruments such as trocars, cannulas, and optical medical devices, including endoscopes, cystoscopes, arthroscopes, laparoscopes, etc., are inserted through small incisions or portals in a patient's body or body cavity and manipulated to perform surgical procedures within the patient.

Minimally invasive surgical procedures are safer than open surgery and result in quicker patient recovery, shorter hospital stays, and lower health care costs. Accordingly, minimizing invasiveness continues to be of importance, and there is a continuing need for devices and methods that achieve this objective.

One area that has benefited from minimally invasive surgical techniques is shoulder surgery. Shoulder surgery has evolved over the last several years from being an open surgical procedure to an arthroscopic surgical procedure. This evolution is the result of technological advances in equipment, instruments and implants.

During surgery, fluid is introduced into the surgical site to expand the joint and control bleeding. A major concern involving arthroscopic surgery of the shoulder is extravasation. Extravasation is the collection of interstitial fluid such as blood, irrigation fluids or medications into tissue surrounding an infusion site. Fluid escaping into the soft tissues of the shoulder and the periscapular region can have adverse effects on the patient. Some of these effects include tracheal compression, the accumulation of blood or clots in the joint (hemarthrosis), the forming of blood clots in veins (thrombophlebitis), arterial injury, nerve injury, the compression of blood vessels and nerves surrounding the joint (compartment syndrome), and infection. These effects cause longer recovery time as well as pain and discomfort in patients. Extravasation occurring during surgery can also cause premature collapse of the surgical field forcing surgeons to rush procedures. Because of the effects caused by extravasation, devices and methods are needed to reduce extravasation during arthroscopic shoulder surgery.

SUMMARY

The devices and methods shown below provide for the minimization of fluid extravasation during arthroscopic surgery. The extravasation minimization device allows a surgeon to drain fluids from the soft tissue surrounding the surgical field while also providing a stable surgical portal for arthroscopic surgical instruments. The extravasation minimization device comprises a tube with outwardly extending ribs extending longitudinally along the tube having drainage lumens disposed therein. Drainage holes in fluid communication with the drainage lumens are disposed in the channels running longitudinally between the outwardly extending ribs. The proximal portion of the extravasation minimization device is provided with a fluid port, a manifold and other means of controlling the flow of fluid inside the extravasation minimization device. The distal tip of the atraumatic extravasation minimization device is arcuate in shape preventing damage to the tissue in the surgical field. Each drainage hole communicates with one or more of the drainage lumens inside the ribs, thereby allowing fluid to flow between the surgical field and sources or sinks located outside the patient. The extravasation minimization device allows the surgeon to reduce the amount of fluid extravasation occurring in surrounding tissue while preserving a surgical portal.

DETAILED DESCRIPTION OF THE INVENTIONS

Figure 1:
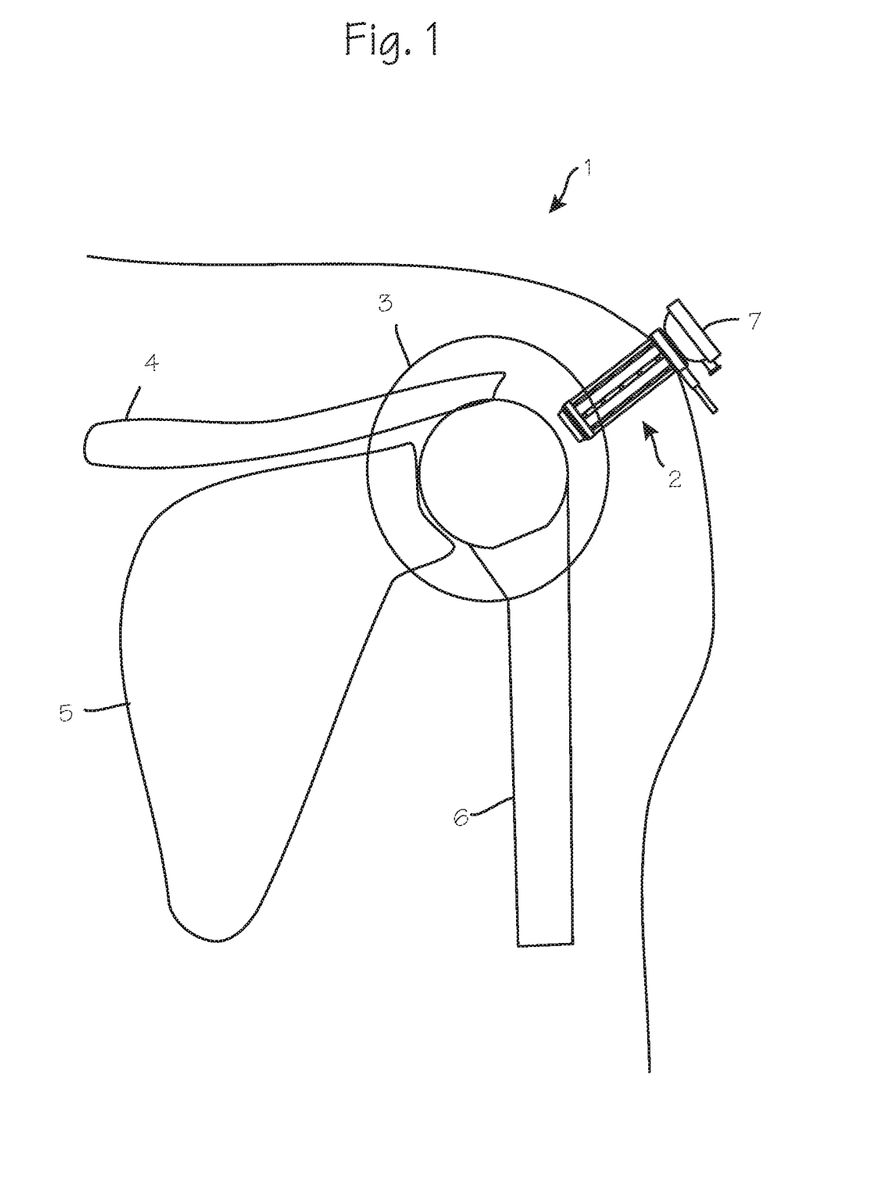
FIG. 1 illustrates a method of performing arthroscopic surgery on a patient using the extravasation minimization device.

FIG. 1 illustrates a method of performing arthroscopic surgery on a patient's shoulder 1 using the extravasation minimization device 2. The extravasation minimization device is shown inserted into the joint capsule 3 of a shoulder of a patient. Various anatomical landmarks are depicted including the patient's clavicle 4, scapula 5 and humerus 6. An arthroscopic instrument 7 is disposed within the extravasation minimization device.

During arthroscopic shoulder surgery, the surgeon introduces the arthroscope into the shoulder via a first portal in order to visualize the surgical field. A trimming instrument is introduced through a second portal to remove or trim tissue that the surgeon determines should be removed or trimmed. Optionally, an irrigating instrument may be introduced through a third portal in order to distend the joint, and/or irrigate the surgical field to maintain a clear view.

Figure 2:
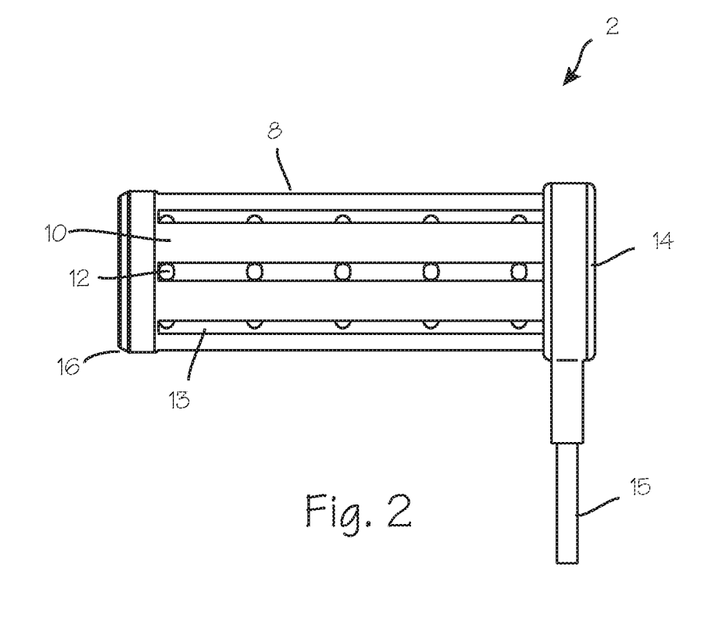
FIG. 2 is a side view of an extravasation minimization device.
Figure 3:
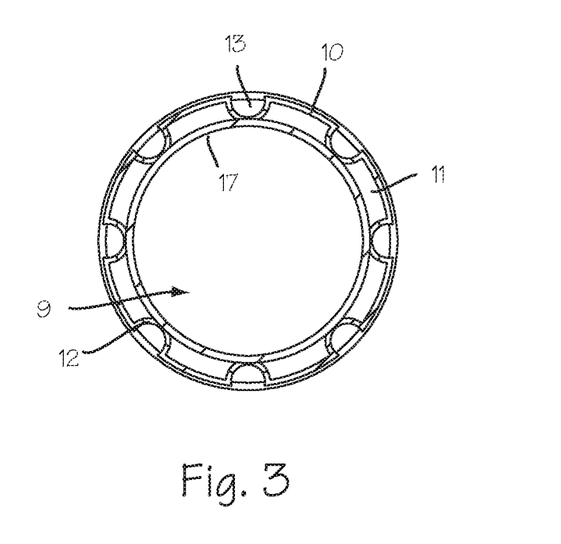
FIG. 3 is a radial cross-sectional view of the extravasation minimization device.

FIG. 2 illustrates a side view of an extravasation minimization device 2 while FIG. 3 is a cross-sectional view of the extravasation minimization device 2. The extravasation minimization device 2 comprises a sleeve 8 of resilient material having a central lumen 9 extending therethrough. The central lumen 9 is sized and dimensioned to accommodate cannulas and arthroscopic surgical instruments such as arthroscopes, endoscope, awl, pick, shaver, etc. The extravasation minimization device 2 further comprises a plurality of outwardly extending ribs 10 Extending longitudinally along the sleeve 8. Drainage lumens 11 are disposed within the ribs. A plurality or drainage apertures 12 is disposed in channels 13 or flutes between the outwardly extending ribs 10. The drainage apertures 12 are in fluid communication with the drainage lumens 11 disposed within the ribs 10. The ribs 10 support tissue away from the apertures 12 when the device is used during surgery. The proximal portion of the extravasation minimization device is provided with a manifold 14 or other adapter. The manifold or adapter provides for the removal of fluid from the drainage lumens 11 through operable use of a vacuum source or sink of wicking material. The manifold is placed in fluid communication with the drainage lumens 11 and a fluid port 15. The fluid port is placed in fluid communication with a vacuum source. The manifold 14 or fluid port 15 may be provided with or coupled to other means of controlling the flow of fluid and or the amount of suction inside the extravasation minimization device. The means for controlling suction and fluid flow may include valves, switches and computer based control systems. The distal tip 16 of the sleeve 8 is arcuate in shape preventing damage to tissue in the surgical field. Each drainage aperture 12 is in fluid communication with one or more of the drainage lumens 11 disposed within the ribs 10, thereby allowing fluid to flow between the surgical field and vacuum sources or sinks located outside the patient.

The extravasation minimization device may be manufactured from sterilizable biocompatible polymers such as nylon, polycarbonate urethane, polyurethane, polydimethylsiloxane and polyethylene glycol. As depicted in the cross-sectional view in FIG. 3, the outward extending ribs 10 are provided with the drainage lumens. The longitudinal channels 13 have an arcuate cross-section. Typically, the extravasation minimization device has an outer diameter of approximately 0.25 inches. The central lumen 9 is sized and dimensioned to accommodate the outer diameter of arthroscopic surgical instruments. The sleeve friction fits over the outer surface of the arthroscopic instrument when the sleeve 8 is disposed about the arthroscopic instrument. Drainage apertures 12 in fluid communication with the drainage lumens 11 may also disposed along the inner diameter 17 of the central lumen of the extravasation minimization device.

Figure 4:
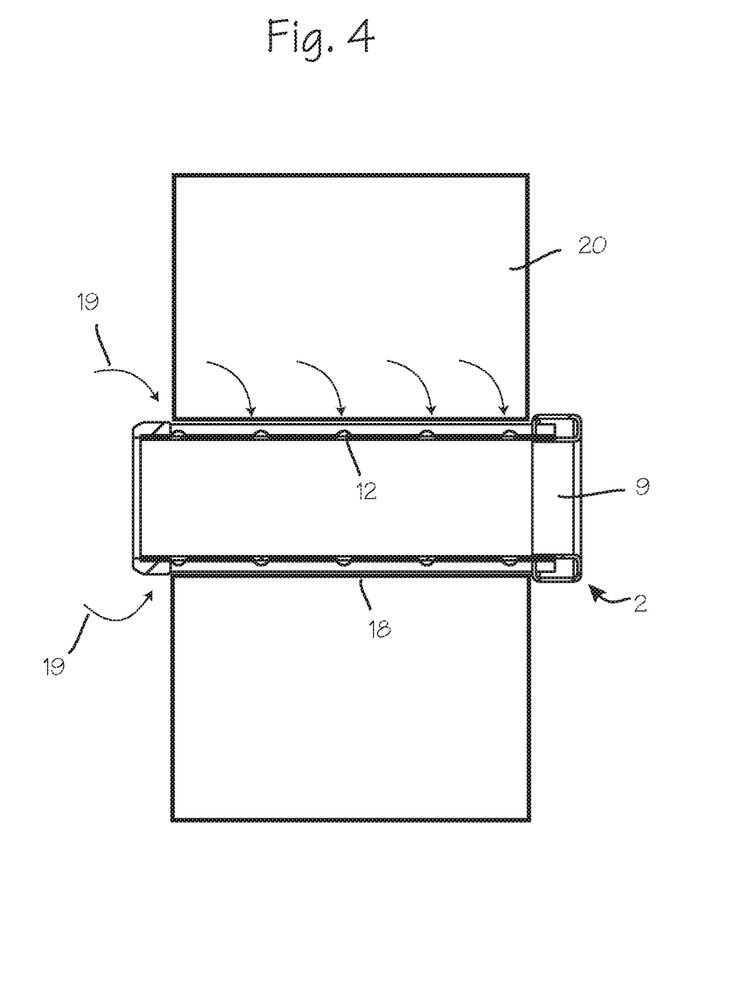
FIG. 4 is a longitudinal sectional view of the extravasation minimization device in shoulder tissue.

FIG. 4 shows a sectional view of the extravasation minimization device 2 in shoulder tissue. The device is disposed within a surgical portal 18 created by a surgeon in a patient. The central lumen 9 allows the extravasation minimization device 2 to be disposed about an arthroscopic cannula device. During arthroscopic surgical procedures, pressurized fluid is used to distend the joint, irrigate the surgical site and disrupt tissue bleeding. The pressurized fluid, blood and debris 19 are drained from shoulder tissue 20 surrounding the surgical site through drainage apertures. The device 2 drains excess fluid passing out of a surgical site into surrounding soft tissues in the shoulder. Removal of fluid, blood and debris reduces the amount of fluid left in the shoulder tissue thereby minimizing extravasation.

Figure 5:
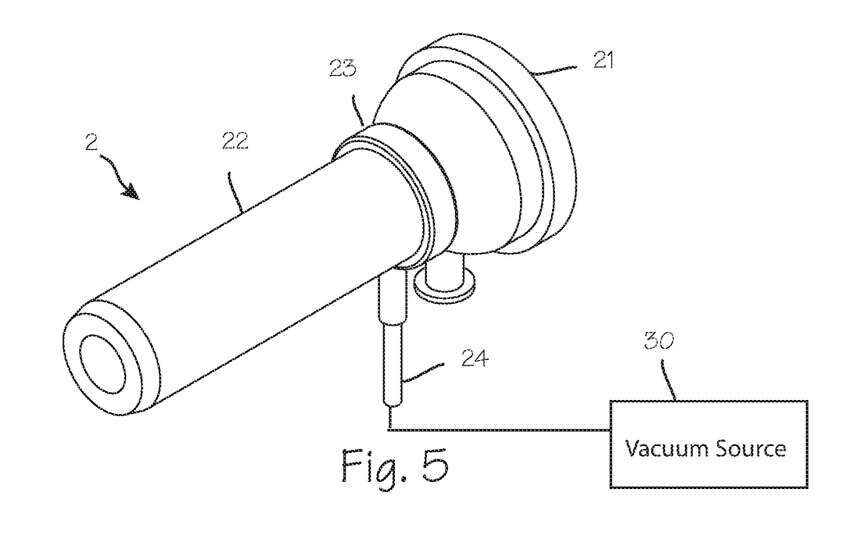
FIG. 5 is an alternative configuration of the extravasation minimization device.

FIG. 5 depicts an alternative configuration of the extravasation minimization device 2 having an arthroscopic cannula 21 disposed therein. Here, the extravasation minimization device 2 comprises a sleeve 22 of wicking material such as medical grade open-cell foam, fabric, or felt. The foam, felt, or fabric can be manufactured from polyolefin, polyurethane, polyester, silicone, expanded PTFE, nylon, or other suitable medical grade material. This sleeve 22 of wicking material functions as a wick or conduit to channel excess pressurized fluid into a proximal collection manifold 23 and away from the tissue surrounding a surgical site. A fluid port 24 in fluid communication with the manifold 23 allows fluid to flow to a vacuum source 30 or collection sink outside the patient. The sleeve may also be manufactured from a laminate that provides both a non-stick outer surface and drainage of excess fluid through wicking or capillary action.

The extravasation minimization device absorbs fluid preferentially relative to the surrounding muscle tissue. This prevents extravasation, the collection of interstitial fluid into the tissue. The extravasation minimization device can operate by capillary action or be used in conjunction with a vacuum source operably connected to a manifold or adapter coupled to the proximal end of the sleeve. The vacuum source removes fluid from the wicking material preventing its saturation. The sleeve is manufactured from material with sufficient stiffness to prevent collapse and occlusion.

Figure 6:
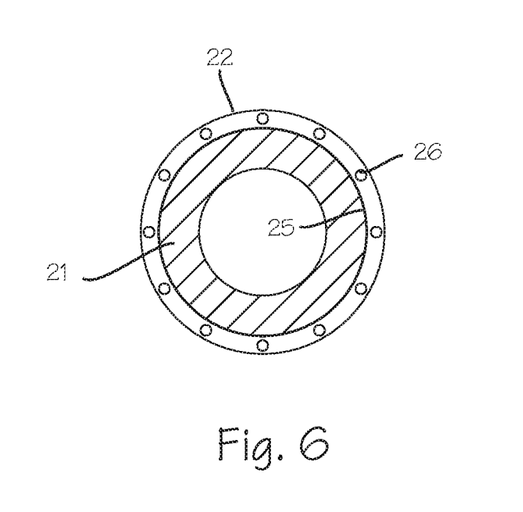
FIG. 6 is a cross-sectional view of an extravasation minimization device having drainage lumens provided within a sleeve.
Figure 7:
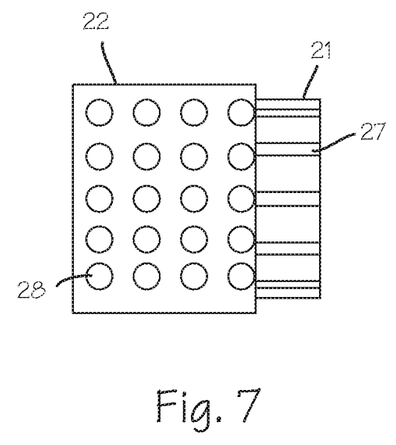
FIG. 7 illustrates a detailed view of an extravasation minimization device having fenestrations disposed about a cannula with exterior grooves.
Figure 8:
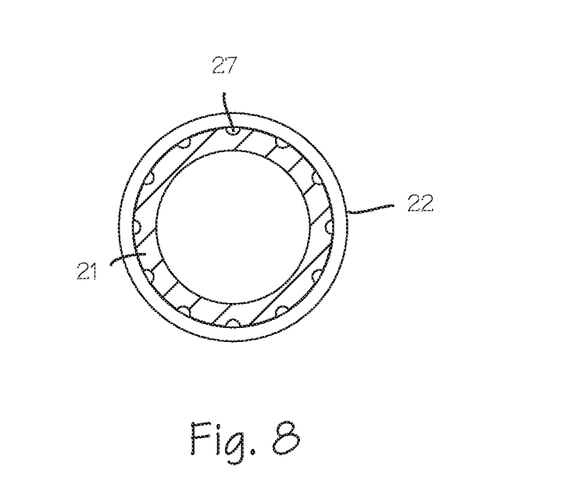
FIG. 8 is a cross-sectional view of an extravasation minimization device disposed about a cannula with exterior grooves.
Figure 9:
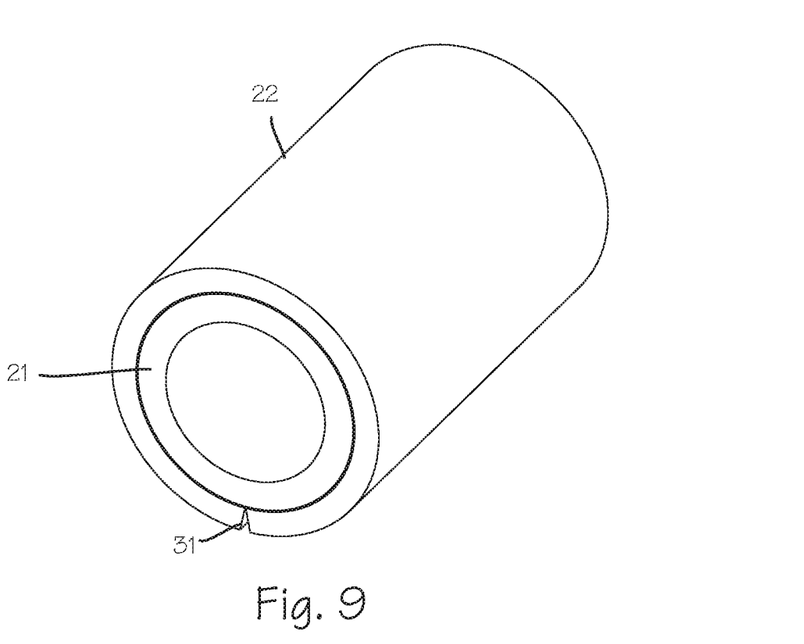
FIG. 9 is an extravasation minimization device having a "C" channel sleeve.
Figure 10:
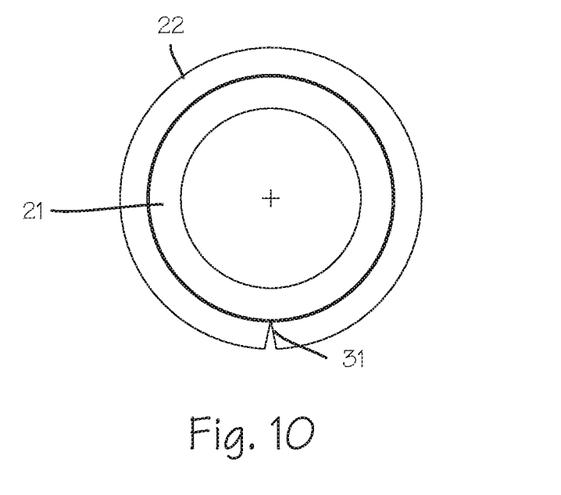
FIG. 10 is a radial cross-sectional view of the extravasation minimization device having a "C" channel sleeve.

As shown in FIG. 6, the sleeve 22 contains a central lumen 25 sized and dimension to friction fit over an arthroscopic shoulder cannula 21 or other surgical device. To aid in the transfer of fluid along the length of the wicking, drainage lumens 26 or channels running longitudinally may be provided within the sleeve 22. These channels may alternatively be formed by longitudinal grooves 27 in the outer surface of the cannula 21 as shown in FIG. 7 and FIG. 8. The sleeve 22 may be manufactured from an open cell foam having a smooth exterior surface such as self-skinning foam or be manufactured from a lamination construction of permeable and impermeable layers. The laminate sleeve has an outer layer of non-stick material comprising a thin polyester heat shrink tube allowing smooth entry into tissue while preventing adhesion to the tissue. A plurality of fenestrations 28 in the outer layer of non-stick material allow the passage of fluid from the soft tissue surrounding a surgical site to open cell foam comprising an inner core of the self-skinning foam or laminate. In addition to a friction fit configuration, the sleeve 22 can be manufactured in a "C-clip" configuration as shown in FIGS. 9 and 10. Here, the radial cross section of the sleeve 22 of wicking material is in substantially the shape of a "C." The sleeve is disposed about the outer surface of arthroscopic cannula 21 by using the longitudinal slit 31 in the sleeve to place the cannula within the sleeve.

Figure 11:
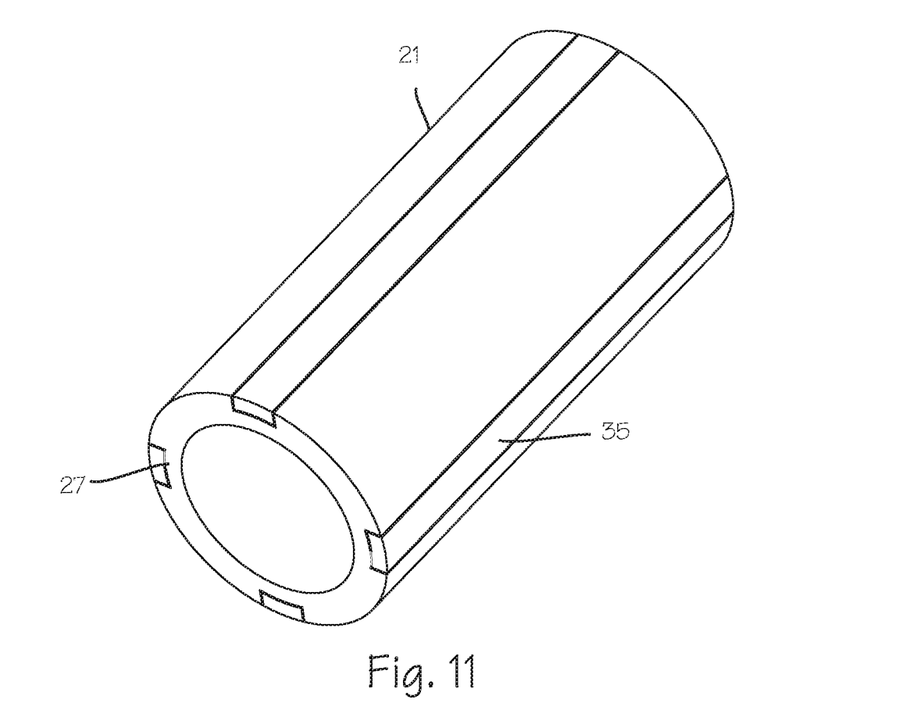
FIG. 11 is an extravasation minimization device provided with one or more strips of wicking material disposed about the outer surface of a cannula.
Figure 12:
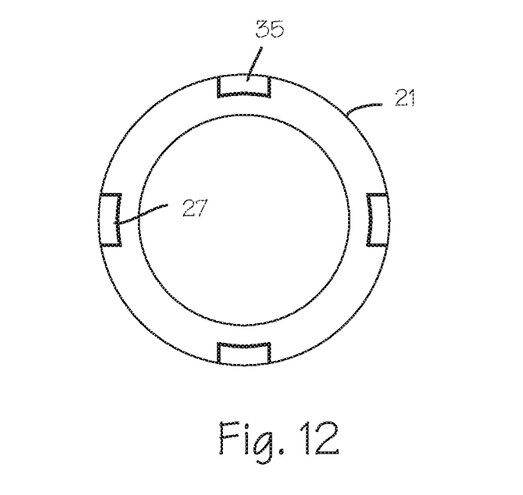
FIG. 12 is a radial cross-sectional view of the extravasation minimization device provided with one or more strips of wicking material disposed about the outer surface of a cannula.

The extravasation minimization device 2 can be provided as one or more strips of wicking material disposed about the outer surface of a cannula 21. In FIG. 11 and FIG. 12, the outer surface of an arthroscopic cannula is provided with one or more longitudinal grooves 27 or flutes. Strips 35 of wicking material are disposed within the grooves. The strips are placed in fluid communication with a sink or vacuum source to prevent the wicking material from becoming saturated. A manifold or other fluid adapter disposed on the proximal end of the arthroscopic cannula provides for fluid communication between the wicking material and vacuum source.

Figure 13:
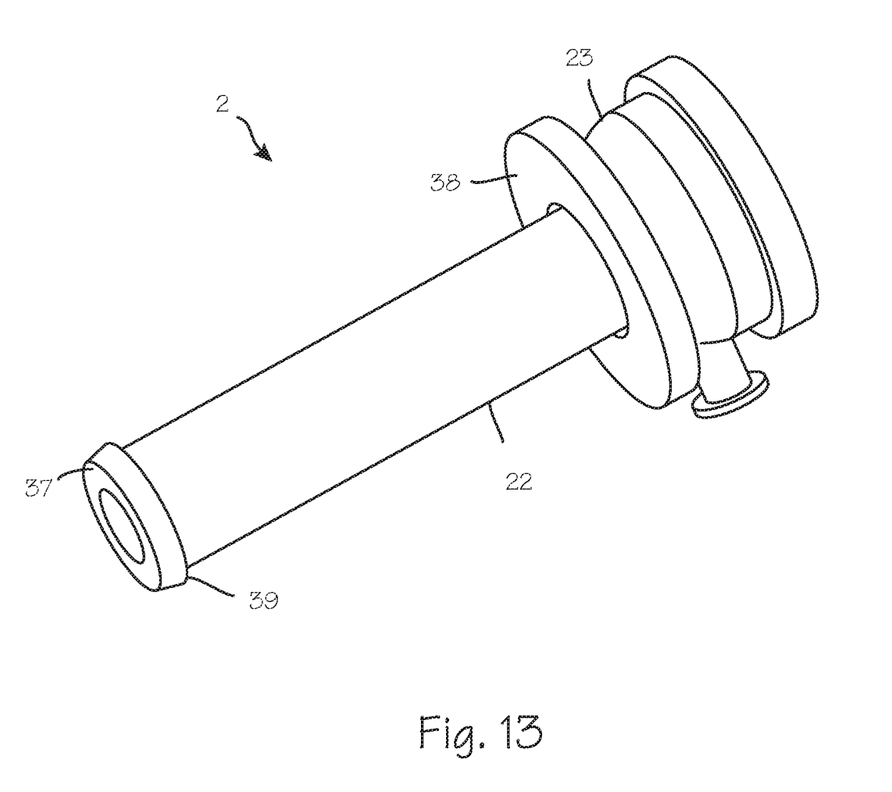
FIG. 13 is an extravasation minimization device with a retention tip and a slidable grommet.

As illustrated in FIG. 13, the extravasation minimization device 2 can be provided with a retention tip 37 and a sliding foam grommet 38. Here, the sleeve 22 of wicking material has a retention tip 37 at the distal end of the sleeve 22 having an outer diameter larger than the outer diameter of the body of sleeve. The retention tip 37 can be frustoconical or arcuate in shape to facilitate entry into a surgical portal while preventing injury to the patient. The retention tip 37 creates a flange 39 that extends outward from the outer diameter of the sleeve 22. A slidable grommet 38 is tightly disposed about the outer diameter of the sleeve 22. When in use, the sleeve 22 disposed about an arthroscopic cannula 21 is inserted into a surgical portal. Tissue surrounding the portal can then be compressed between the flange 39 of the retention tip and the grommet 38 by sliding the grommet 38 down the sleeve. Compressing the tissue between the flange 39 and grommet forces fluid out of the tissue and into the wicking material. Excess fluid is removed from the sleeve 22 of wicking material using an adapter or manifold 23 at the proximal end of the sleeve 22 in fluid communication with the sleeve 22. The adapter is operably connected to a vacuum source to drain fluid.

The extravasation minimization device 2 can be part of a complete fluid management system comprising a fluid source, vacuum source, arthroscopic surgical pump and control system. An over pressure valve can be operably coupled to the extravasation minimization device 2 to allow a drainage lumen 26 in the device to open and drain the joint if the joint is over-pressurized by an arthroscopic pump.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A device for minimizing extravasation comprising:
   a sleeve characterized by a distal end and proximal end having a central lumen sized and dimensioned to be removably disposed over an arthroscopic instrument, said central lumen having an inner diameter;
   a plurality of outwardly extending longitudinal ribs disposed over the exterior of the sleeve having drainage lumens disposed therein;
   a plurality of drainage apertures in fluid communication with the drainage lumens, said drainage apertures disposed along the inner diameter of the central lumen; and
   a manifold disposed on the proximal end of the sleeve in fluid communication with the drainage lumens;
   wherein the plurality of drainage apertures permit excess fluid to be removed from tissue surrounding a surgical site.

2. The device of claim 1 further comprising a vacuum source in fluid communication with the manifold.

3. The device of claim 1 further comprising a sink in fluid communication with the manifold.

4. A method of performing arthroscopic surgery, said method comprising the steps of:
   providing an extravasation minimization device, said device comprising:
      a sleeve characterized by a distal end and proximal end having a central lumen sized and dimensioned to be removably disposed over an arthroscopic instrument, said central lumen having an inner diameter;
      a plurality of outwardly extending longitudinal ribs disposed over the exterior of the sleeve having drainage lumens disposed therein;
      a plurality of drainage apertures in fluid communication with the drainage lumens, said drainage apertures disposed along the inner diameter of the central lumen; and
      a manifold disposed on the proximal end of the sleeve in fluid communication with the drainage lumens;
      wherein the plurality of drainage apertures permit excess fluid to be removed from tissue surrounding a surgical site;
   providing an arthroscopic instrument suitable for performing an arthroscopic surgical procedure;
   placing the arthroscopic instrument inside of the extravasation minimization device; and
   performing an arthroscopic surgical procedure.

5. The method of claim 4 further comprising providing a vacuum source in fluid communication with the manifold.

6. The method of claim 4 further comprising providing a sink in fluid communication with the manifold.

7. A device for minimizing extravasation comprising:
   a cannula characterized by a distal end, a proximal end, an outer surface, and having a central lumen sized and dimensioned to be removably disposed over an arthroscopic instrument;
   a plurality of longitudinal grooves disposed over the exterior of the cannula;
   a sleeve of wicking material disposed over the outer surface of the cannula, wherein the sleeve of wicking material further comprises a plurality of fenestrations disposed on an outer surface of the sleeve; and
   an adapter disposed on the proximal end of the cannula in fluid communication with the sleeve of wicking material;
   wherein the wicking material permits excess fluid to be removed from tissue surrounding a surgical site.

8. The device of claim 7 further comprising a vacuum source in fluid communication with the adapter.

9. The device of claim 7 wherein the adapter is a manifold.

10. A method of performing arthroscopic surgery, said method comprising the steps of:
    providing an extravasation minimization device, said device comprising:
       a cannula characterized by a distal end, a proximal end, an outer surface, and having a central lumen sized and dimensioned to be removably disposed over an arthroscopic instrument;
       a plurality of longitudinal grooves disposed over the exterior of the cannula;
       a sleeve of wicking material disposed over the outer surface of the cannula, wherein the sleeve of wicking material further comprises a plurality of fenestrations disposed on an outer surface of the sleeve; and
       a manifold disposed on the proximal end of the cannula in fluid communication with the sleeve of wicking material;
       wherein the wicking material permits excess fluid to be removed from tissue surrounding a surgical site;
    providing an arthroscopic instrument suitable for performing an arthroscopic surgical procedure;

placing the arthroscopic instrument inside of the extravasation minimization device; and performing an arthroscopic surgical procedure.

11. The method of claim 10 further comprising providing a vacuum source in fluid communication with the manifold.

12. The method of claim 10 further comprising providing a sink in fluid communication with the manifold.

\* \* \* \* \*